US012656345B2

(12) United States Patent
Yoshihara et al.

(10) Patent No.: US 12,656,345 B2
(45) Date of Patent: Jun. 16, 2026

(54) METHOD FOR DIAGNOSING HUMAN T-CELL LEUKEMIA VIRUS TYPE 1 (HTLV-1)-RELATED DISEASE

(71) Applicants: NEC CORPORATION, Tokyo (JP); UNIVERSITY OF THE RYUKYUS, Nakagami-gun (JP)

(72) Inventors: Yoshiko Yoshihara, Tokyo (JP); Takuya Fukushima, Okinawa (JP); Yuetsu Tanaka, Okinawa (JP); Hiroaki Masuzaki, Okinawa (JP); Kennosuke Karube, Okinawa (JP); Naoki Imaizumi, Okinawa (JP)

(73) Assignees: NEC CORPORATION, Tokyo (JP); UNIVERSITY, Okinawa (JP)

( * ) Notice: Subject to any disclaimer, the term of this patent is extended or adjusted under 35 U.S.C. 154(b) by 1028 days.

(21) Appl. No.: 17/774,395

(22) PCT Filed: Nov. 2, 2020

(86) PCT No.: PCT/JP2020/041000
§ 371 (c)(1),
(2) Date: May 4, 2022

(87) PCT Pub. No.: WO2021/090786
PCT Pub. Date: May 14, 2021

(65) Prior Publication Data
US 2022/0404363 A1 Dec. 22, 2022

(30) Foreign Application Priority Data
Nov. 5, 2019 (JP) ................................. 2019-200986

(51) Int. Cl.
*G01N 33/569* (2006.01)
*G01N 33/68* (2006.01)

(52) U.S. Cl.
CPC ... *G01N 33/56988* (2013.01); *G01N 33/6872* (2013.01)

(58) Field of Classification Search
CPC ......... G01N 33/56988; G01N 33/6872; G01N 2800/50; G01N 2333/15; G01N 33/57426;
(Continued)

(56) References Cited

U.S. PATENT DOCUMENTS

2012/0094934 A1 4/2012 Collard et al.

FOREIGN PATENT DOCUMENTS

JP 2004-163121 A 6/2004
JP 2005-147798 A 6/2005
(Continued)

OTHER PUBLICATIONS

Gasper-Smith et al. Induction of plasma (TRAIL), TNFR-2, Fas ligand, and plasma microparticles after human immunodeficiency virus type 1 (HIV-1) transmission: implications for HIV-1 vaccine design. J Virol. Aug. 2008;82(15):7700-10. (Year: 2008).*
(Continued)

*Primary Examiner* — Christopher L Chin
*Assistant Examiner* — Ellis Follett Lusi
(74) *Attorney, Agent, or Firm* — Sughrue Mion, PLLC

(57) ABSTRACT

As a technique enabling to simply and accurately diagnose human T cell leukemia virus type 1 (HTLV-1) related disease, there is provided a diagnostic method for an HTLV-1 related disease based on an amount of tumor necrosis factor receptor 2 (TNFR2) in a blood sample taken from a subject, wherein (1) it is determined based on an increase of the amount of TNFR2 that the subject suffers from, or is likely to develop, the HTLV-1 related disease; and/or (2) it is determined based on a decrease of the amount
(Continued)

of TNFR2 that the subject is in remission, or is likely to be in remission, of the HTLV-1 related disease.

3 Claims, 1 Drawing Sheet

(58) Field of Classification Search
CPC ...... G01N 2333/7151; C07K 14/70578; C07K 14/7151
USPC ...................... 435/7.24, 6.14, 7.1, 7.23, 7.92
See application file for complete search history.

(56) References Cited

FOREIGN PATENT DOCUMENTS

| | | |
|---|---|---|
| JP | 2008-292474 A | 12/2008 |
| JP | 2009-254357 A | 11/2009 |
| JP | 2013-007742 A | 1/2013 |
| JP | 2014-059298 A | 4/2014 |
| JP | 2014-059299 A | 4/2014 |

OTHER PUBLICATIONS

Govindaraj et al. Lenalidomide-based maintenance therapy reduces TNF receptor 2 on CD4 T cells and enhances immune effector function in acute myeloid leukemia patients. Am J Hematol. Aug. 2014;89(8):795-802. (Year: 2014).*

Anguille et al. Dendritic cell vaccination as postremission treatment to prevent or delay relapse in acute myeloid leukemia. Blood. Oct. 12, 2017;130(15):1713-1721. (Year: 2017).*

Wang et al. Increased Regulatory T Cells in Peripheral Blood of Acute Myeloid Leukemia Patients Rely on Tumor Necrosis Factor (TNF)-α-TNF Receptor-2 Pathway. Front Immunol. Jun. 5, 2018;9:1274. (Year: 2018).*

Noh Jin Park, et al., "Measurement of Cetuximab and Panitumumab-Unbound Serum EGFR Extracellular Domain Using an Assay Based on Slow Off-Rate Modified Aptamer (SOMAmer) Reagents", PLOS, Aug. 2013, pp. 1-7, vol. 8, Issue 8.

Yingjie Nie, et al., "Blockade of TNFR2 signaling enhances the immunotherapeutic effect of CpG ODN in a mouse model of colon cancer", Sci Signal, Apr. 15, 2021, pp. 1-20.

Camina Louise Hugo Guerrero, et al., "Proteomic profiling of HTLV-1 carriers and ATL patients reveals sTNFR2 as a novel diagnostic biomarker for acute ATL", Blood Advances, Mar. 24, 2020, pp. 1062-1071, vol. 4, No. 6.

International Search Report for PCT/JP2020/041000 dated Jan. 21, 2021 [PCT/ISA/210].

Extended European Search Report issued Oct. 19, 2023 in Application No. 20884216.1.

Nabila Ei Kramani, et al., "Tumor Necrosis Factor Receptor 2: Its Clinical Significance and Clinicopathologic Correlation in acute leukemias", Journal of Applied Pharmaceutical Science, Nov. 2015, vol. 5, No. 11, 079-083 (5 pages).

Alexander Ungewickell, et al., "Genomic analysis of mycosis fungoides and Sézary syndrome identifies recurrent alterations in TNFR2", Nature Genetics, Sep. 2015, vol. 47, No. 9, 1056-1060 (7 pages).

Yan Wen Zhang, et al., "Expression of tumor necrosis factor receptor 2 in human non-small cell lung cancer and its role as a potential prognostic biomarker", Thoracic Cancer, 2019, vol. 10, 437-444 (8 pages).

Chie Nishioka, et al., "Serum level of soluble CD30 correlates with the aggressiveness of adult T-cell leukemia/lymphoma", Cancer Science, Nov. 2005, vol. 96, No. 11, 810-815 (6 pages).

N. Goto, et al. "Serum-soluble tumor necrosis factor receptor 2 (sTNF-R2) level determines clinical outcome in patients with aggressive non-Hodgkin's lymphoma" European Journal of Haematology, 2006, vol. 77, pp. 217-225 (9 pages).

Masayuki Matsuda, et al. "Increased levels of soluble tumor necrosis factor receptor in patients with multiple sclerosis and HTLV-1-associated myelopathy", Journal of Neuroimmunology, vol. 52, 1994, pp. 33-40 (8 pages).

Taiwanese Office Action dated Aug. 29, 2023 in Application No. 109138396.

* cited by examiner

| Carrier vs Acute | Carrier vs Chronic | Carrier vs Smoldering | Carrier vs Lymphoma | Carrier vs Remission |
|---|---|---|---|---|
| 0.000000010 | 0.0305 | 0.0675 | 0.0044 | 0.0826 |
| *** | * | | ** | |
| | Acute vs Chronic | Acute vs Smoldering | Acute vs Lymphoma | Acute vs Remission |
| | 0.065 | 0.000000 | 0.0028 | 0.000009 |
| | | *** | * | *** |
| | | Chronic vs Smoldering | Chronic vs Lymphoma | Chronic vs Remission |
| | | 0.0995 | 0.7514 | 0.1616 |
| | | | Smoldering vs Lymphoma | Smoldering vs Remission |
| | | | 0.0370 | 0.5131 |
| | | | * | |
| | | | | Lymphoma vs Remission |
| | | | | 0.0927 |

$p < 0.05 = *$
$p < 0.01 = **$
$p < 0.001 = ***$

| Carrier vs ATL | |
|---|---|
| 0.0000000001 | or ~1.06E-10 |
| *** | |

METHOD FOR DIAGNOSING HUMAN T-CELL LEUKEMIA VIRUS TYPE 1 (HTLV-1)-RELATED DISEASE

CROSS REFERENCE TO RELATED APPLICATIONS

This application is a National Stage of International Application No. PCT/JP2020/041000 filed Nov. 2, 2020, claiming priority based on Japanese Patent Application No. 2019-200986 filed Nov. 5, 2019.

TECHNICAL FIELD

The present invention relates to a method for diagnosing human T-cell leukemia virus type 1 (HTLV-1) associated diseases, more specifically, a method and kit for diagnosing HTLV-1 related diseases using a blood marker protein.

BACKGROUND ART

Human T-cell leukemia virus type 1 (HTLV-1) is a retrovirus principally infects CD4-positive T cells to cause adult T-cell leukemia (ATL). HTLV-1 also causes HTLV-1 associated myelopathy (HAM) and HTLV-1 uveitis (HU). Hereinafter ATL, HAM and HU will be collectively referred to as "HTLV-1 related diseases".

ATL is a malignant hematological tumor that invades various organs throughout the body and categorized into 4 disease forms: acute form, lymphoma-form, chronic form and smoldering form. The acute and lymphoma forms, which are also referred to "aggressive ATL", are hematopoietic malignancies with the poorest prognosis. Whereas, the chronic and smoldering forms, which are also referred to as "indolent ATL", mostly develop into blast crisis during the time course of the disease. The prognosis of these forms is poor.

As a treatment for ATL, a combination chemotherapy is known. However, even in a current report, the median survival time of "aggressive ATL" still remains 13 months, which and not satisfactory. Patients with "Indolent ATL", in some cases, survive for a long time without treatment and are mostly monitored without treatment until the disease worsens due to blast crisis and the like.

Currently, a main infection route of HTLV-1 is considered as a mother-to-child transmission, particularly through mother milk. HTLV-1 related diseases are developed from individuals infected with HTLV-1 (HTLV-1 careers) but most of the careers are asymptomatic. Japan is only one country having a high prevalence of HTLV-1 among the developed countries. HTLV-1 careers and HTLV-1 related diseases are often seen in the southwest of Japan including Kyushu and Okinawa districts.

In connection with the present invention, Patent Literature 1 discloses "a diagnostic agent for adult T-cell leukemia, containing a reagent that can detect the presence or absence of a transcript of TSLC1 gene or TSLC1 protein in cells or serum". The TSLC1 gene is considered as a gene specifically expressed in leukemia cells taken from ATL patients. Owing to the technique disclosed there, it is reported that T cell leukemia can be highly precisely diagnosed.

The tumor necrosis factor (TNF) superfamily is a multifunctional proinflammatory cytokine superfamily activating signaling pathways for cellular survival, apoptosis, inflammatory response and cell differentiation. Cellular response to TNF is induced via two receptors, i.e., TNFR2 (also referred to as TNF Receptor-2 or CD120b) and TNFR1 (also referred to as TNF Receptor-1 or CD120a). Of the two receptors, TNFR2 is mainly expressed in immune cells and activated by both $TNF\alpha$ and $TNF\beta1$. When TNFR2 binds to $TNF\alpha$ or $TNF\beta1$, TNFR2 is released from a cell surface and $TNF\alpha$ or $TNF\beta1$ dissociates from TNFR2 released. It is reported that a combination use of a TNFR2 inhibitor and an immunostimulant can be an effective therapy for a certain type of cancer.

CITATION LIST

Patent Literature

Patent Literature 1: Japanese Patent Laid-Open No. 2005-147798

Non Patent Literature

Non Patent Literature 1: "Measurement of Cetuximab and Panitumumab-Unbound Serum EGFR Extracellular Domain Using an Assay Based on Slow Off-Rate Modified Aptamer (SOMAmer) Reagents", NJ Park et al., PLOS ONE, 2013, 8 (4): e61002.

Non Patent Literature 2: "Blockade of TNFR2 signaling enhances the immunotherapeutic effect of CpG ODN in a mouse model of colon cancer.", Y. Nie, et al., Sci. Signal, 2018, 11 (511), eaan0790

SUMMARY OF INVENTION

Technical Problem

Compared to Kyushu and Okinawa districts where many experienced ATL specialist physicians and core hospitals are present, in metropolitan areas such as Kanto and Kinki districts, even though the real numbers of HTLV-1 careers and ATL patients are equal to those in a high prevalence area of HTLV-1, the number of specialist physicians capable of diagnosing ATL is low at present.

In the circumstances, a main object of the present invention is to provide a technique that can realize a simple and accurate diagnosis of an HTLV-1 related disease.

Solution to Problem

To attain the object, the present invention provides the following [1] to [31].

[1] A diagnostic method for a human T cellular leukemia virus type 1 (HTLV-1) related disease based on an amount of tumor necrosis factor receptor 2 (TNFR2) in a blood sample taken from a subject, comprising
(1) determining, based on an increase of the amount of TNFR2, that the subject suffers from, or is highly likely to develop, the HTLV-1 related disease.

[2] The method according to [1], comprising the steps of:
measuring an amount of TNFR2 in blood samples taken from the subject at two or more different time points; and
(1) determining that, if an amount of TNFR2 measured at a later time point is significantly high compared to an amount of TNFR2 measured at an earlier time point, the subject suffers from, or is highly likely to develop, the HTLV-1 related disease.

[3] The method according to [1] or [2], wherein
(1) it is determined that, if the amount of TNFR2 is as high as a value beyond a predetermined reference value, the subject suffers from, or is likely to develop, the HTLV-1 related disease.

[4] The method according to any one of [1] to [3], wherein the subject is an HTLV-1 carrier.

[5] The method according to any one of [1] to [4], wherein the HTLV-1 related disease is adult T-cell leukemia (ATL).

[6] The method according to [5], wherein the HTLV-1 related disease is acute ATL.

[7] The method according to any one of [1] to [6], wherein the blood sample is blood plasma.

[8] A diagnostic method for an HTLV-1 related disease based on an amount of TNFR2 in a blood sample taken from a subject, comprising (2) determining, based on a decrease of the amount of TNFR2, that the subject is in remission, or is likely to be in remission, of the HTLV-1 related disease.

[9] The method according to [8], comprising the steps of: measuring an amount of TNFR2 in blood samples taken from the subject at two or more different time points; and (2) determining that, if an amount of TNFR2 measured at a later time point is significantly low compared to an amount of TNFR2 measured at an earlier time point, the subject is in remission, or is highly likely to be in remission, of the HTLV-1 related disease.

[10] The method according to [8] or [9], wherein (2) it is determined that, if the amount of TNFR2 decreases from a value beyond a predetermined reference value to a value below the predetermined reference value, the subject is in remission, or is highly likely to be in remission, of the HTLV-1 related disease.

[11] The method according to any one of [8] to [10], wherein the HTLV-1 related disease is ATL.

[12] The method according to [11], wherein the HTLV-1 related disease is acute ATL.

[13] The method according to any one of [8] to [12], wherein the subject is a patient with acute ATL or a patient with an HTLV-1 related disease having a history of acute ATL.

[14] The method according to [13], wherein the patient with an HTLV-1 related disease is a patient diagnosed to suffer from acute ATL based on the amount of TNFR2 beyond the reference value in a blood sample.

[15] The method according to any one of [8] to [14], wherein the blood sample is blood plasma.

[16] A diagnostic kit for an HTLV-1 related disease, containing a reagent for detecting TNFR2.

[17] The diagnostic kit according to [16], wherein the HTLV-1 related disease is ATL.

[18] The diagnostic kit according to [16] or [17], wherein the detection reagent is an antibody, nucleic acid or aptamer that specifically binds to TNFR2.

[19] Use of TNFR2 for diagnosing an HTLV-1 related disease.

[20] Use according to [19], wherein the HTLV-1 related disease is ATL.

[21] A method for determining effectiveness of a treatment for an HTLV-1 related disease based on an amount of TNFR2 in a blood sample taken from a subject, wherein (2) a decrease in the amount of TNFR2 decreases indicates the effectiveness of the treatment.

[22] The method according to [21], comprising the steps of:

measuring an amount of TNFR2 in blood samples taken from the subject at two or more different time points; and (2) determining that, if the amount of TNFR2 measured at a later time point is significantly low compared to the amount of TNFR2 measured at an earlier time point, the treatment is effective.

[23] The method according to [22], wherein (2) it is determined that, if the amount of TNFR2 decreases from a value beyond a predetermined reference value to a value below the predetermined reference value, the treatment is effective.

[24] The method according to any one of [21] to [23], wherein the HTLV-1 related disease is ATL.

[25] The method according to [24], wherein the HTLV-1 related disease is acute ATL.

[26] The method according to any one of [21] to [25], wherein the subject is a patient with an HTLV-1 related disease having a history of acute ATL.

[27] The method according to [26], wherein the patient with an HTLV-1 related disease is a patient diagnosed to suffer from acute ATL based on the amount of TNFR2 beyond the reference value, in a blood sample.

[28] The method according to any one of [21] to [27], wherein the blood sample is blood plasma.

[29] A method for treating an HTLV-1 related disease, comprising the steps of:

measuring an amount of TNFR2 in blood samples taken from a subject at two or more different time points;

(1) selecting the subject as a treatment subject, if the amount of TNFR2 measured at a later time point is significantly high compared to the amount of TNFR2 measured at an earlier time point, and applying a chemotherapy and/or a non-chemotherapy to the treatment subject selected.

[30] A method for treating an HTLV-1 related disease, comprising the steps of:

measuring an amount of TNFR2 in blood samples taken from a subject at two or more different time points, and (2) reducing, stopping or terminating application of a chemotherapy and/or a non-chemotherapy to the subject if the mount of TNFR2 measured at a later time point is significantly low compared to the amount of TNFR2 measured at an earlier time point.

[31] The method according to [29] or [30], wherein the non-chemotherapy is a cancer vaccine therapy.

Advantageous Effects of Invention

The present invention provides a technique that can realize a simple and accurate diagnosis of an HTLV-1 related disease. According to the diagnostic method for an HTLV-1 related disease of the present invention, it is possible to determine that the subject suffers from, or is likely to develop, the HTLV-1 related disease, and that the subject is in remission, or is likely to be in remission, of the HTLV-1 related disease after development, and further determine effectiveness of a treatment.

DESCRIPTION OF EMBODIMENTS

Figures 1, 2:
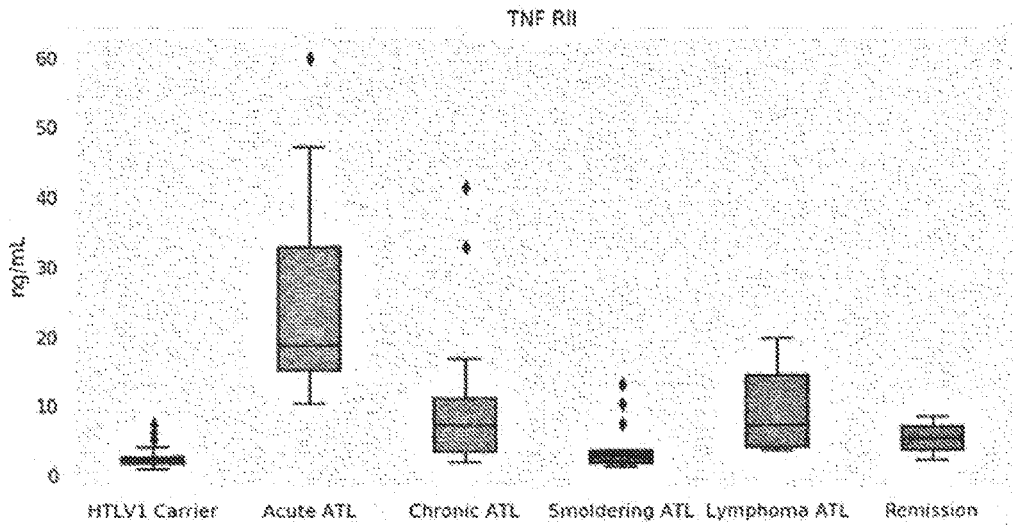
FIG. 1 The figure is a box-and-whisker plot chart showing measured blood-plasma TNFR2 concentrations (ng/ml) of an HTLV-1 carrier group, an acute ATL patient group, a chronic ATL patient group, a smoldering ATL patient group, a lymphoma ATL patient group and a patient group in remission.
FIG. 2 The figure is a chart showing significant differences in measured blood-plasma TNFR2 concentration value between groups (an HTLV-1 carrier group, an acute ATL patient group, a chronic ATL patient group, a smoldering ATL patient group, a lymphoma ATL patient group and a patient group in remission) by p values (t-test).

Now, a preferred embodiment for carrying out the present invention will be described. Note that, the following embodiment is a typical embodiment of the present invention and should not be construed as limiting the range of the present invention.

1. Outline of Diagnostic Method for an HTLV-1 Related Disease 1-1. Diagnosis of Onset In an embodiment of the diagnostic method for an HTLV-1 related disease according to the present invention, it is characterized in that whether a subject suffers from, or is likely of developing an HTLV-1 related disease can be determined based on an increase of the amount of TNFR2 in a blood sample taken from the subject.

Examples of the HTLV-1 related disease include not only ATL but also HTLV-1 associated myelopathy (HAM) and HTLV-1 uveitis (HU). The HTLV-1 related disease is preferably ATL, more preferably acute ATL, chronic ATL and lymphoma ATL, and particularly preferably, acute ATL.

The blood TNFR2 concentration is significantly high in HTLV-1 related disease patient groups (ATL patient groups, particularly, an acute ATL patient group, a chronic ATL patient group and a lymphoma ATL patient group), compared to an HTLV-1 carrier group.

Accordingly, if an increase of the amount of TNFR2 in blood is used as a reference, it can be determined that the subject suffers from, or is likely to develop, an HTLV-1 related disease.

More specifically, for example, the amount of TNFR2 in a blood sample taken from a subject (preferably, HTLV-1 carrier) at two or more different time points is measured, and then, if the amount of TNFR2 measured at a later time point is significantly high compared to the amount of TNFR2 measured at an earlier time point, it can be determined that the subject suffers from, or is highly likely to develop, an HTLV-1 related disease.

1-2. Remission Diagnosis

In another embodiment of the diagnostic method for an HTLV-1 related disease according to the present invention, it is characterized in that whether the subject is in remission, or is likely to be in remission, of the HTLV-1 related disease is determined based on a decrease of the amount of TNFR2 in a blood sample taken from a subject.

The blood TNFR2 concentration significantly decreases in a group of patients in remission compared to HTLV-1 related disease patient groups (ATL patient groups, particularly, acute ATL patient group).

Accordingly, if a decrease of the amount of TNFR2 in blood is used as a reference, whether the subject is in remission, or is likely to be in remission, of an HTLV-1 related disease, can be determined.

More specifically, for example, the amount of TNFR2 in blood samples taken from a subject (preferably, acute ATL patient) at two or more different time points is measured, and then, if the amount of TNFR2 measured at a later time point is significantly low compared to the amount of TNFR2 measured at an earlier time point, it can be determined that the subject is in remission, or is highly likely to be in remission, of an HTLV-1 related disease.

Note that, in the present invention, the "onset" includes not only a first onset but also recurrence after remission, and the "remission" includes not only first remission but also re-remission after recurrence.

2. Measurement Step 2-1. Subject for Diagnosing Onset

In the diagnostic method for an HTLV-1 related disease according to the present invention, when it is determined that a subject suffers from, or is likely to develop, the HTLV-1 related disease, the subject is preferably an HTLV-1 carrier. The HTLV-1 career can be selected in accordance with a known method in the technical field.

For example, the HTLV-1 career can be selected by detecting the presence or absence of an anti-HTLV-1 antibody in blood, for example, by PA (gelatin particle aggregation) method, CLEIA (chemiluminescent enzyme immunoassay) method or western blot.

The HTLV-1 career can be selected, for example, by detecting the presence or absence of insertion of HTLV-1 in the genome by southern blot.

2-2. Subject for Remission Diagnosis

In the diagnostic method for an HTLV-1 related disease according to the present invention, when it is determined that a subject is in remission, or is likely to be in remission, of an HTLV-1 related disease, the subject is preferably an ATL patient, more preferably a patient with acute ATL or a patient with a history of ATL, and further preferably, a patient diagnosed to suffer from acute ATL based on the blood level of TNFR2 beyond a reference value (described later).

2-3. Measurement Method

The blood sample taken from a subject may be whole blood, serum or plasma.

The TNFR2 protein to be measured may be a full-length protein or a fragment thereof. The full-length protein or a fragment thereof may be a membrane-bound protein or a free (unbound) protein. The free protein may be insoluble or soluble.

The "full-length protein" refers to a protein having a naturally occurring amino acid sequence, which is the same as expressed in vivo, or a mutant thereof. The fragment thereof may have a part of the amino acid sequence of a full-length protein, having a length of, for example, 5 to 10, 11 to 20, 21 to 30, 31 to 40, or 41 to 50 amino acids. The amino acid length may be 51 or more.

The amount of a marker protein (TNFR2) in a blood sample can be measured by a method known in the technical field and using a detection reagent such as an antibody or a fragment thereof (e.g., F(ab), F(ab)2, F(ab)' and Fv fragment), a nucleic acid or an aptamer (nucleic acid aptamer or peptide aptamer) that specifically binds to the protein.

A preferable measurement method is ELISA (enzyme-linked immunosorbent assay) using an antibody.

The antibody may be a monoclonal or a polyclonal antibody and may belong to any one of the classes of IgG, IgM, IgA, IgD and IgE.

The methods for preparing these detection reagents are known in the technical field. Proper detection reagents are commercially available.

The detection reagent is preferably tagged with a label detectable by an optical, magnetic or electrical means.

The detection reagent is preferably labeled with a fluorescent substance having an excitation wavelength and emission wavelength suitably detected by a commercially available fluorescence analyzer. Examples of the fluorescence substance include phycoerythrin (PE), fluorescein isothio-cyanate (FITC), rhodamine (RH), Texas Red (TX), Cy3, Hoechst 33258, and 4',6-diamizino-2-phenyl indole (DAPI).

When a fluorescently labeled detection reagent is used, first, the detection reagent is allowed to bind to a solid phase. Then, a blood sample is brought into contact with the solid phase, reacted and washed, as needed. Fluorescence emitted from the fluorescent label of a marker protein held on the solid phase via the detection reagent, is detected. Based on the intensity thereof, the amount of protein can be determined.

The amount of the marker protein in a blood sample can be measured by, for example, LC/MS (liquid chromatography/mass spectrometry).

The amount of the marker protein can be measured by using an entrusted protein measurement service, for example, SOMAscan, provided by a company, SomaLogic.

A kit for diagnosing an HTLV-1 related disease according to the present invention can be contain not only a detection reagent as mentioned above but also various reagents for use in the measurement methods mentioned herein.

The amount of marker protein can be measured once or a plurality of times at intervals with respect to the same subject.

3. Determination Step 3-1. Determination of Onset

When the amount of TNFR2 is measured at two or more different time points, if the amount of TNFR2 measured at a later time point is significantly high compared to the amount of TNFR2 measured at an earlier time point, it can be determined that the subject suffers from, or is highly likely to develop, an HTLV-1 related disease.

For example, for a subject who is an HTLV-1 carrier and has not yet suffered from an HTLV-1 related disease, the amount of TNFR2 is measured. Thereafter, the amount of TNFR2 of the same subject is measured. If the amount significantly increases at this time, it is determined that the subject has already suffered from, or is highly likely to develop, an HTLV-1 related disease.

When the amount of TNFR2 is measured for the same subject a plurality of times at intervals, the accuracy of the determination can be improved by taking a time dependent change in TNFR2 amount into consideration.

More specifically, if a time-dependent increase of TNFR2 in amount is observed, it is determined that the subject suffers from, or is more highly likely to develop, an HTLV-1 related disease. If the amount sharply increases with time, the subject can be diagnosed to develop a blast crisis.

When the amount of TNFR2 is measured at two or more different time points and only once, if the amount of TNFR2 increases to a value beyond a predetermined reference value, it can be determined that the subject suffers from, or is more highly likely to develop, an HTLV-1 related disease.

An average, median or mode of measured values obtained in blood samples of, for example, an HTLV-1 carrier group or a healthy subject group (not HTLV-1 career), can be employed as the reference value.

If the amount of TNFR2 is increased to the reference value or more, preferably higher than the reference value by 1-5%, more preferably 6-10%, further preferably 11-25%, and most preferably 26-50%, it is determined that the subject suffers from, or is likely to develop, the HTLV-1 related disease. As the amount is significantly higher than the reference value, the determination accuracy improves. Because of this, if desired, a value higher than the reference value by 51% or more may be used as an indicator.

When comparison is made between an HTLV-1 carrier group and an acute ATL patient group, a particularly significant increase of TNFR2 concentration is observed and the range of TNFR2 concentration in the carrier group is not overlapped with that in the acute ATL patient group (see, Examples). Accordingly, if a value within the non-overlap range is used as a reference value (threshold), it is possible to determine or predict that an HTLV-1 carrier suffer from acute ATL. The reference value can be a blood concentration within the range of, for example, 5-15 ng/ml or 7.5-12.5 ng/ml, more specifically, a value within the range of 7.6-10.3 ng/ml, preferably 8-10 ng/ml, and more preferably 8.5-9.5; more specifically, can be 8, 8.5, 9, 9.5 or 10 ng/ml, preferably 8, 9 or 10 ng/ml, and more preferably 9 ng/ml.

3-2. Determination of Remission

When the amount of TNFR2 is measured at two or more different time points, if the amount of TNFR2 measured at a later time point is significantly low compared to the amount of TNFR2 measured at an earlier time point, it can be determined that the subject is in remission, or is highly likely to be in remission, of an HTLV-1 related disease. Furthermore, if the subject had a treatment for an HTLV-1 related disease during the period between the time points, a significant decrease of the amount of TNFR2 indicates the effectiveness of the treatment.

For example, when the amount of TNFR2 of a subject, who is already diagnosed to suffer from an HTLV-1 related disease by the above onset determination, is measured after the onset determination, if the amount of TNFR2 significantly decreases, it can be determined that the subject is in remission, or is highly likely to be in remission, of the HTLV-1 related disease. Furthermore, if the subject had a treatment for the HTLV-1 related disease during the period between the time points, a significant decrease in the amount of TNFR2 indicates that the treatment is effective.

When the amount of TNFR2 is measured for the same subject a plurality of times at intervals, the accuracy of the determination can be improved by taking a time dependent change in TNFR2 amount into consideration.

More specifically, if a time-dependent decrease of TNFR2 in amount is observed, it is determined that the subject is in remission, or is more highly likely to be in remission, of an HTLV-1 related disease.

When the amount of TNFR2 is measured at two or more different time points and only once, if the amount of TNFR2 decreases from a value beyond a predetermined reference value to a value below the reference value, it can also be determined that the subject is in remission, or is highly likely to be in remission, of an HTLV-1 related disease. If the subject received a treatment for the HTLV-1 related disease, a decrease in TNFR2 amount to a value below the reference value indicates the effectiveness of the treatment.

As the reference value, an average, median or mode of measured values obtained in blood samples of, for example, HTLV-1 related disease patient groups, can be employed.

If the amount of TNFR2 is below the reference value, preferably lower than the reference value by 1-5%, more preferably 6-10%, further preferably 11-25%, and most preferably 26-50%, it is determined that the subject is in remission, or is highly likely to be in remission, of an HTLV-1 related disease. As the amount is significantly lower than the reference value, the determination accuracy improves. Because of this, if desired, a value lower than the reference value by 51% or more may be used as an indicator.

The range of TNFR2 concentration detected in the acute ATL patient group is not overlapped with that in a patient group in remission (see, Examples). Accordingly, if a value within the non-overlap range is used as a reference value (threshold), it is possible to detect or predict that an acute ATL patient or a patent having a history of acute ATL is in remission. The reference value can be a blood concentration within the range of, for example, 6-15 ng/ml or 8-12.5 ng/ml, more specifically, a value within the range of 8.4-10.3 ng/ml, preferably 8.5-10 ng/ml, more preferably 9-9.5 ng/ml; more specifically 8.5, 9, 9.5 or 10 ng/ml, preferably 9 or 10 ng/ml, and more preferably 9 ng/ml.

A statistical analysis method or machine learning can be used for determination.

Particularly, discriminant analysis using training data is preferably used. When two groups (for example, the HTLV-1 carrier group and the ATL patient group) are discriminated, linear discriminant analysis is mostly sufficient. However, linear discriminant analysis is limited in application because it is based on the assumption that the population variances of individual groups are equal.

Accordingly, when discriminant analysis is carried out using more complicated data, non-linear discriminant analysis or discriminant analysis using machine learning is desirably used. Examples of the non-linear discriminant analysis include discriminant analysis based on Mahalanobis' generalized distance. Examples of the discrimination analysis using machine learning include k-nearest neighbor algorithm, Naive Bayes classifier, decision tree, neural network, support vector machine, and ensemble learning such as a bagging method, a boosting method and a random forest method. Such a method has been developed in the field of pattern recognition, and findings in the pattern recognition can be applied to the present invention.

In addition, even if an analysis method using no training data, such as principal component analysis, hierarchical clustering, non-hierarchical clustering, and self-organizing map, is employed, discrimination can be made by performing analysis in combination with the subject's data on status of an HTLV-1 related disease previously known.

4. Method for Treating HTLV-1 Related Disease

The diagnostic method for an HTLV-1 related disease according to the present invention can be applied to a method for treating a subject (selected as a treatment subject) who already determined to suffer from, or be highly likely to develop, an HTLV-1 related disease. The treatment method comprises a step of applying a chemotherapy and/or a non-chemotherapy to the selected treatment subject.

More specifically, application of a treatment is quickly started for a treatment subject selected as having an HTLV-1 related disease or having a high possibility of developing the disease.

To a treatment subject determined to have an HTLV-1 related disease or have a higher possibility of developing the disease, or to a treatment subject determined to have a possibility of developing a blast crisis, based on the observation that a time dependent change in amount of TNFR2 is large or sharp, an advanced therapy, such as allogeneic hematopoietic stem cell transplantation, T cell therapy, cancer vaccine therapy and cytokine therapy, is started in combination with or in place of a multi-drug chemotherapy.

In the cancer vaccine therapy, a peptide vaccine or a dendritic cell vaccine can be applied.

For these therapies, immune checkpoint inhibitors can be used in combination.

When the method for diagnosing an HTLV-1 related disease according to the present invention is applied as a therapeutic method, the application of a chemotherapy and/ or a non-chemotherapy to a treatment subject, who has been determined to be in remission of an HTLV-1 related disease or have a high possibility of achieving a remission of the disease, can be reduced, stopped or terminated, or conversely increased, to induce a remission without fail. On the contrary, the application of a chemotherapy and/or a non-chemotherapy to a treatment subject, who has not yet been determined to be in remission of an HTLV-1 related disease or have a high possibility of achieving a remission of the disease, can be increased or another treatment can be applied in place. Note that, a radiation therapy is included in the non-chemotherapy.

EXAMPLE

Test Example 1: Analysis of Plasma Protein of ATL Patient

TNFR2 plasma concentrations of HTLV-1 carriers (30 carriers), ATL patients (69 patients) and 4 individuals in remission of ATL were measured by a commercially available ELISA kit (Quantikine ELISA (registered trademark) Human TNF RII/TNFRSF1B Immunoassay, R&D Systems). In the patients with ATL, 31 patients with acute ATL, 9 patients with lymphoma, 16 patients with chronic ATL and 13 patients with smoldering ATL are included. The plasmas of HTLV-1 careers (hereinafter referred to as a "carrier group"), ATL patients and individuals having a remission of ATL were provided by the Okinawa Bio Information Bank (ATL/HTLV-1 biobank) of Ryukyu University.

The results are shown in FIG. 1 and FIG. 2. FIG. 1 shows measured blood-plasma TNFR2 concentration values (ng/ ml) of an HTLV-1 carrier group, an acute ATL patient group, a chronic ATL patient group, a smoldering ATL patient group, a lymphoma ATL patient group and a patient group in remission. In the figure, plots represent measured values of individual patients. FIG. 2 shows significant differences of the measured values between groups: the HTLV-1 carrier group, acute ATL patient group, chronic ATL patient group, smoldering ATL patient group, lymphoma ATL patient group and patient group in remission, by p values (t-test).

A significant increase of TNFR2 concentration was observed in the acute ATL patient group (p<0.001), chronic ATL patient group (p<0.05) and lymphoma ATL patient group (p<0.01), compared to the HTLV-1 carrier group. When comparison was made between an HTLV-1 carrier group and an acute ATL patient group, a particularly significant increase of TNFR2 concentration was observed, and the range of TNFR2 concentration detected in the carrier group is not overlapped with that detected in the acute ATL patient group. Accordingly, a blood-plasma TNFR2 concentration was considered particularly useful as a marker for detecting that an HTLV-1 carrier patient developed acute ATL. A maximum value of the TNFR2 concentration detected in the HTLV-1 carrier group was 7.54 ng/ml, whereas a minimum value of the TNFR2 concentration detected in the acute ATL patient group was 10.39 ng/ml. From this, it was considered that a value within the range of 7.6-10.3 ng/ml is appropriate as the threshold (reference value) discriminating the two groups.

When comparison is made between the acute ATL patient group and the remission group, a significant decrease in TNFR2 concentration was observed (p<0.001). The range of TNFR2 concentration detected in the acute ATL patient group was not overlapped with that of the remission group. Accordingly, it was considered that the blood-plasma TNFR2 concentration is useful as a marker detecting remission of ATL in an acute ATL patient. A minimum value of TNFR2 concentration detected in the acute ATL patient group was 10.39 ng/ml, whereas a maximum value of TNFR2 concentration detected in the patient group in remission was 8.39 ng/ml. From this, it was considered that a value within the range of 8.4-10.3 ng/ml is appropriate as the threshold (reference value) discriminating the two groups.

The invention claimed is:

1. A method for treating a human T cellular leukemia virus type 1 (HTLV-1) related disease, which is acute adult T-cell leukemia (acute ATL), in a subject suspected of having acute ATL or at risk of developing acute ATL, comprising the steps of:

(1) measuring an amount of tumor necrosis factor receptor 2 (TNFR2) in blood samples taken from the subject suspected of having acute ATL or at risk of developing acute ATL at two or more different time points before applying a therapy for treating acute ATL;

(2) selecting the subject as a treatment subject when the amount of TNFR2 measured at a later time point before applying the therapy for treating acute ATL is higher than the amount of TNFR2 measured at an earlier time point before applying the therapy for treating acute ATL and higher than a blood concentration threshold of 7.6-10.3 ng/ml; and (3) applying the therapy for treating acute ATL to the treatment subject, wherein the therapy is a chemotherapy and/or a non-chemotherapy, and wherein the non-chemotherapy is an allogeneic hematopoietic stem cell transplantation, a T cell therapy, a cancer vaccine therapy or a cytokine therapy.

2. The method according to claim 1 further comprising the step of:

(4) reducing, stopping or terminating application of the therapy for treating acute ATL to the treatment subject if an amount of TNFR2 measured at a later time point after the application of the therapy for treating acute ATL is significantly lower than an amount of TNFR2 measured at an earlier time point after the application of the therapy for treating acute ATL.

3. The method according to claim 1, wherein the blood sample is blood plasma.

* * * * *